(12) United States Patent
Strandberg

(10) Patent No.: US 6,192,276 B1
(45) Date of Patent: Feb. 20, 2001

(54) PACER HOUSING

(75) Inventor: Hans Strandberg, Sundbyberg (SE)

(73) Assignee: Pacesetter AB, Jarfalla (SE)

( * ) Notice: Under 35 U.S.C. 154(b), the term of this patent shall be extended for 0 days.

(21) Appl. No.: 09/381,307

(22) PCT Filed: Mar. 10, 1998

(86) PCT No.: PCT/SE98/00424

§ 371 Date: Sep. 17, 1999

§ 102(e) Date: Sep. 17, 1999

(87) PCT Pub. No.: WO98/42408

PCT Pub. Date: Oct. 1, 1998

(30) Foreign Application Priority Data

Mar. 25, 1997 (SE) .................................................. 9701105

(51) Int. Cl.[7] .................................................. A61N 1/375
(52) U.S. Cl. .............................................. 607/36; 607/37
(58) Field of Search ........................................ 607/36, 37

(56) References Cited

U.S. PATENT DOCUMENTS 5,683,433 * 11/1997 Carson .................................... 607/36
6,112,121 * 8/2000 Paul et al. ............................... 607/37

FOREIGN PATENT DOCUMENTS 0 339 877 11/1989 (EP) .
0 587 379 3/1994 (EP) .

* cited by examiner

*Primary Examiner*—Scott M. Getzow
(74) *Attorney, Agent, or Firm*—Schiff Hardin & Waite

(57) ABSTRACT

A pacemaker housing has a socket for receiving a plug of an electrode lead, the socket being located in an opaque part of the housing, and the housing having an exterior marking which indicates a proper insertion depth for the plug into the socket. The plug of the electrode lead can be provided with one or more markings which successively proceed toward the side of the housing having the socket opening therein, with one of the markings coinciding with the edge of the socket when the plug is inserted to a proper depth into the socket.

10 Claims, 1 Drawing Sheet

PACER HOUSING

BACKGROUND OF THE INVENTION

1. Field of the Invention

The present invention relates to pacer housings and more particularly to those parts of the housing intended for connection to the electrode leads.

2. Description of the Prior Art

Implantable pacers normally comprise a pacer housing (also called can) containing electronic circuitry and a unit for electric power as well as different electrodes which are connected to the interior parts in the pacer housing and which are to be implanted in or in the vicinity of the heart. The electrodes are connected to the pacer by means of leads. The internal parts of the pacers have to be well protected against the internal environment, especially the body fluids in the body for a long period of time, which places strict requirements on all entries into the interior of the can and especially on the connections of the leads to the housing. At the same time it should be possible to disconnect the pacer from the implanted leads for replacement or servicing of the pacer. The connective parts of the pacer and the leads have largely been standardized so as to encompass a relatively deep female socket comprising a number of contact surfaces whereas the leads are provided with a male part comprising one or several corresponding peripheral, generally circular contact surfaces.

When a pacemaker is being implanted, it is important that the physician is able to ascertain that the proximal ends of the electrode leads are fully inserted so as to ensure that respective contact surfaces fully are in engagement. It furthermore is important that the male part of the leads can be securely locked in the female part socket in the pacer housing when all connections have been made.

At present these problems in most cases are addressed by making the connective part of the pacer housing containing the female socket of a transparent material, normally epoxy resin, which is molded onto the housing and onto contacts extending outwardly from the housing. The male part of the leads is normally locked by means of set screws, although other fastening means are known. By these means the physician is able to determine visually whether the male contact part of the lead has been fully inserted into the female socket before tightening the set screws. The positioning and alignment of the different contact surfaces and of the fastening means or metallic threads for the set screws prior to the moulding of the connective part is however very complicated and the delay in the manufacturing process incurred by the curing of the epoxy resin is considerable.

It would thus be desirable if the molding procedure could be dispensed with.

SUMMARY OF THE INVENTION

It is an object of the present invention to provide a pacemaker housing and a lead therefore which avoid the need to have a molded-on header composed of transparent material.

This object is achieved in accordance with the principles of the present invention in a pacemaker housing having a socket adapted to receive a proximal end of an electrode lead, the lead having an electrode disposed at the distal end thereof, and wherein the socket is located in an opaque part of the housing with the socket having an opening at a side of the housing, and wherein the housing has exterior markings indicating an appropriate insertion depth for the plug into the socket.

These markings can indicate the direction of the socket and/or the location of the socket, and the markings can correspond to (represent) the shape of a longitudinal section of the socket.

The plug of the electrode lead can be provided with scale marks at an exterior thereof for facilitating a determination of the insertion depth of the plug. As the plug is inserted into the aforementioned socket, the scale marks successively move toward the side of the housing having the socket opening, and the plug is pushed into the socket until a scale mark corresponding to the depth of the socket coincides with the edge of the socket opening.

DESCRIPTION OF THE PREFERRED EMBODIMENTS

Figure 1:
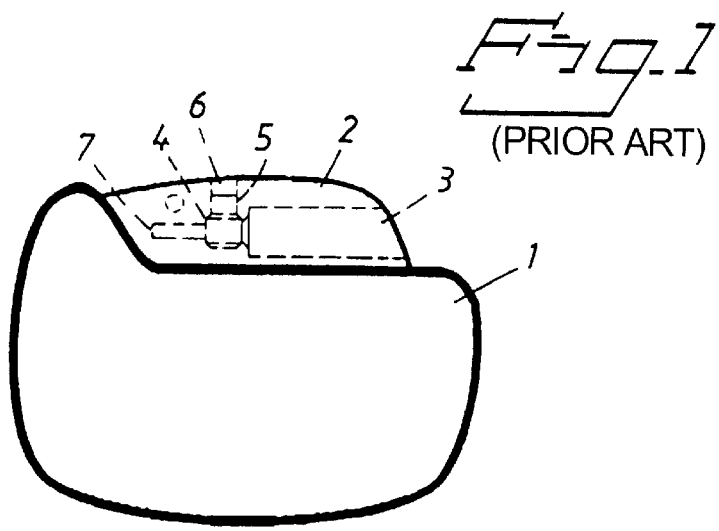
FIG. 1 shows a conventional pacer housing with a transparent, molded connective part.

FIG. 1 illustrates a conventional housing 1 having a molded, transparent connective part 2. The connective part 2 includes a female socket 3. The inner end of the socket 3 is provided with a longitudinal bore 7 having a relatively small diameter. The bore 7 is provided with a contact surface 4 adjacent to which threads 5 for a set or lock screw are located in a bore 6 oriented orthogonally relative to the female socket.

Figure 2:
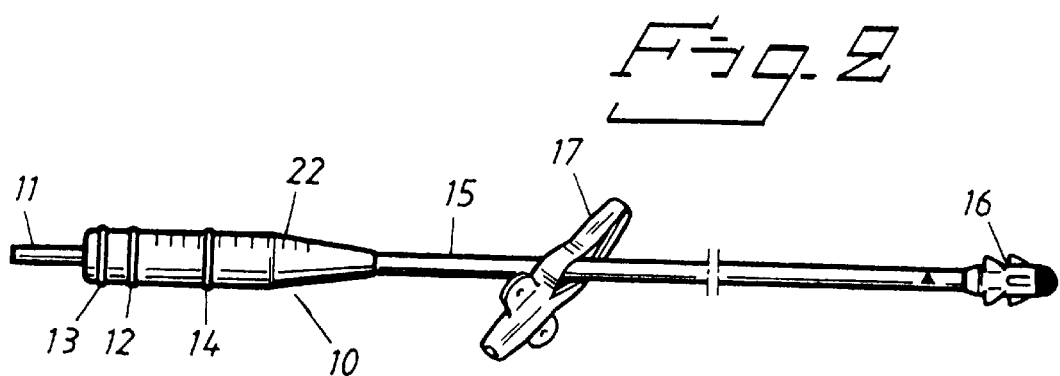
FIG. 2 shows a lead with a male connective part in accordance with the present invention.

FIG. 2 illustrates a lead 15 comprising a proximal connecting plug 10 and a distal, transvenous, intracardial electrode 16 as well as an attachment element 17 for suturing the proximal end of the lead in the body of the patient. The connecting plug 10 is designed to be received in the socket 3 and the end thereof is provided with a longitudinally projecting contact pin 11 as well as a cylindrical body 17 provided with sealing rings 12, 13, 14 intended to engage and seal against the corresponding inner cylindrical surface of the female socket 3. The shape of the pin 11 corresponds to the shape of the bore 7. When the plug 10 is inserted into the socket 3 the pin 11 engages the contact surface 4 and the set screw in the bore 6 can be tightened against the pin 11 in order to securely lock the plug 10 in the socket 3. Since the connective part is made of transparent material, the physician easily can determine whether the plug 10 has been fully inserted and that the pin 11 is in contact with the contact surface 4. The complexities involved in holding the bores, contact surfaces and threads in position and keeping them open and free from the moulding material during the moulding process are evident.

Figure 3:
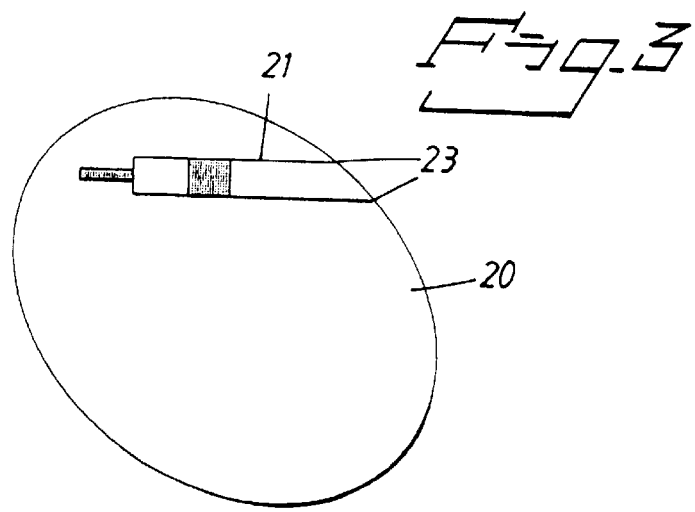
FIG. 3 shows a pacer housing designed in accordance with the present invention.

According to the invention these complexities are avoided in a pacer designed with a socket located inside the metal housing and which consequently cannot be seen from the outside of the housing. Such a pacer is shown in FIG. 3. These kinds of sockets are sometimes termed "black holes". The outside of the metal housing 20 is provided with markings 21 showing the depth of the socket, the markings beginning at the side edge 23 of the pacer housing. When the physician intends to connect the lead to the pacer, it is only necessary to place the plug 10 so that it coincides with the marking 21 on the housing. The plug may be provided with scale marks 22 by which means the depth of the socket may be determined by reading the scale marks against the edge 23 of the housing (which corresponds to the edge of the socket), the plug then simply being pushed into the socket until the scale mark corresponding to the depth of the socket coincides with the edge of the socket corresponding to the aforementioned edge as defined by the side of the housing. At this point the plug will be fully inserted into the socket. Alternatively the plug may be grasped with the hand or with a tool at the point corresponding to the edge of the socket as measured against the marking on the housing and pushed into the socket until the hand or tool engages the side of the housing. The plug will then be fully inserted in the socket.

The determination of whether the plug has been fully inserted into the housing and that electrical connection has been obtained may be complemented with known indicator arrangements, such as light emitting diodes which are activated upon contact or an ECG which changes upon contact. In a preferred embodiment of the invention, however, the housing has a marking on the exterior thereof which is a representation of the longitudinal cross-sectional shape of the socket and is located on the housing so as to fully correspond with the location and direction of the socket. By this means the contour of the pacer housing in the vicinity will be taken into account when the depth of insertion of the plug is determined.

The markings on the housing may be made by engraving using a laser or otherwise, by etching etc.

Although modifications and changes may be suggested by those skilled in the art, it is the intention of the inventor to embody within the patent warranted hereon all changes and modifications as reasonably and properly come within the scope of his contribution to the art.

I claim as my Invention:

1. In a pacemaker housing having a socket adapted to receive a plug of an electrode, said housing having an opaque portion and said socket being located in said opaque portion and having a socket opening at a side of said housing, the improvement comprising:

markings at an exterior of said housing indicating an insertion depth for the plug into the socket.

2. A pacemaker housing as claimed in claim 1 wherein said markings indicate a direction of said socket.

3. A pacemaker housing as claimed in claim 2 wherein said markings indicate a location of said socket.

4. A pacemaker housing as claimed in claim 3 wherein said markings comprise a representation of a shape of a longitudinal section of said socket.

5. An electrode lead having a plug adapted to be received in a socket in a side of a pacemaker housing, said plug comprising:

a plug element having an exterior surface; and at least one scale mark disposed on said exterior surface of said plug element said scale mark moving increasingly closer to a side of said housing as said plug element is inserted into said housing, and being disposed at a distance from a tip of said plug element so that when said plug element is properly inserted in said socket, said scale mark substantially coincides with an edge of said housing.

6. A plug as claimed in claim 5 comprising a plurality of scale marks on said exterior of said plug element.

7. A pacemaker and electrode lead combination comprising:

a pacemaker having a pacemaker housing containing a socket having a socket opening at a side of said housing, said housing having an opaque part in which said socket is located;

an electrode lead having a plug insertable into said socket, said plug having scale marks thereon which successively proceed toward said side of said housing as said plug is inserted into said socket, with one of said scale marks coinciding with an edge of said socket when said plug is properly inserted into said socket; and said pacemaker housing having markings at an exterior thereof indicating a proper insertion depth for said plug into said socket.

8. A combination as claimed in claim 7 wherein said markings indicate a direction of said socket.

9. A combination as claimed in claim 8 wherein said markings indicate a location of said socket.

10. A combination as claimed in claim 9 wherein said markings comprise a representation of a shape of a longitudinal section of said socket.

\* \* \* \* \*